United States Patent
Trussell

(10) Patent No.: US 8,161,973 B2
(45) Date of Patent: Apr. 24, 2012

(54) REVERSIBLE VASECTOMY DEVICE AND METHOD

(75) Inventor: JC Trussell, Hummelstown, PA (US)

(73) Assignee: The Penn State Research Foundation, University Park, PA (US)

( * ) Notice: Subject to any disclaimer, the term of this patent is extended or adjusted under 35 U.S.C. 154(b) by 805 days.

(21) Appl. No.: 12/206,132

(22) Filed: Sep. 8, 2008

(65) Prior Publication Data

US 2009/0069827 A1    Mar. 12, 2009

Related U.S. Application Data

(60) Provisional application No. 60/970,633, filed on Sep. 7, 2007, provisional application No. 60/979,978, filed on Oct. 15, 2007.

(51) Int. Cl.
*A61F 6/02* (2006.01)

(52) U.S. Cl. ........ 128/843; 128/842; 606/135; 606/137; 606/153

(58) Field of Classification Search .......... 128/830, 128/831, 842, 843, 887; 604/8, 9, 34, 256, 604/247; 424/430; 606/135, 137, 153–156
See application file for complete search history.

(56) References Cited

U.S. PATENT DOCUMENTS

| | | | |
|---|---|---|---|
| 3,589,355 A | 6/1971 | Lee et al. | |
| 3,613,661 A | 10/1971 | Shah | |
| 3,687,129 A | 8/1972 | Nuwayser | |
| 3,699,957 A | 10/1972 | Robinson | |
| 3,704,704 A | 12/1972 | Gonzales | |
| 3,815,578 A | 6/1974 | Bucalo | |
| 3,831,584 A | 8/1974 | Bucalo | |
| 3,877,435 A | 4/1975 | Bucalo | |
| 3,990,434 A | 11/1976 | Free | |
| 4,013,063 A | 3/1977 | Bucalo | |
| 4,200,088 A | 4/1980 | Denniston, Jr. | |

(Continued)

FOREIGN PATENT DOCUMENTS

WO    WO-9413356    6/1994

OTHER PUBLICATIONS

Brueschke, E.E., L.J.D. Zaneveld, M. Burns, R. Rodzen, J.R. Wingfield, J.H. Maness. "Development of a reversible vas deferens occlusive device. IV. Rigid prosthetic devices." Fertility and Sterility 1975, vol. 26, vol. 1, pp. 29-39.

(Continued)

*Primary Examiner* — Patricia Bianco
*Assistant Examiner* — Keri J Nelson
(74) *Attorney, Agent, or Firm* — Gifford, Krass, Sprinkle, Anderson & Citkowski, P.C.

(57) ABSTRACT

A reversible vasectomy device includes a first and a second connector piece for attachment to the severed ends of the vas deferens. Each connector piece has an outer vas deferens attaching end, an opposite inner end, and a passage from the outer to the inner end. A midpiece has end portions that are connectable to the inner ends of the connector pieces, a passage in one end portion and a vent from the passage to an exterior surface. When the connector pieces are connected to the end portions, the passage in one of the connector pieces is in fluid communication with the vent, but is not in fluid communication with the passage in the other connector piece.

18 Claims, 6 Drawing Sheets

U.S. PATENT DOCUMENTS

| | | | | |
|---|---|---|---|---|
| 4,206,749 A | * | 6/1980 | Bucalo | 128/843 |
| 4,512,342 A | | 4/1985 | Zaneveld et al. | |
| 4,682,592 A | | 7/1987 | Thorsgard | |
| 4,788,966 A | | 12/1988 | Yoon | |
| 5,065,751 A | | 11/1991 | Wolf | |
| 5,471,997 A | | 12/1995 | Thompson | |
| 5,474,089 A | | 12/1995 | Waynant | |

OTHER PUBLICATIONS

Brueschke, E.E., R.A. Kaleckas, J.R. Wingfield, T.J. Welsh, L.J.D. Zaneveld. "Development of reversible vas deferens occlusive device. VII. Physical and microscopic observations after long-term implantation of flexible prosthetic devices." Fertility and Sterility 1980, vol. 33, No. 2, pp. 167-178.

Brueschke, E.E., L.J.D. Zaneveld, R.Rodzen, K. Mayerhofer, M. Burns, J.H. Maness, and J.R. Windfield, "Development of a reversible vas differens occlusive device: v. flexible prosthetic devices." Fertility and Sterility 1975, vol. 26, No. 1, pp. 40-52.

* cited by examiner

REVERSIBLE VASECTOMY DEVICE AND METHOD

REFERENCE TO RELATED APPLICATIONS

This application claims priority from U.S. Provisional Patent Application Ser. Nos. 60/970,633, filed Sep. 7, 2007 and 60/979,978, filed Oct. 15, 2007, the entire content of both of which is incorporated herein by reference.

FIELD OF THE INVENTION

The present invention relates generally to birth control devices and methods and, more specifically, to a device and method for providing a reversible vasectomy.

BACKGROUND OF THE INVENTION

A vasectomy or vas occlusion is a procedure by which the vas deferens of a male are blocked or severed in order to prevent the passage of sperm through the vas deferens. The vas deferens extends from the epididymis, at the testicles, to the abdomen where it normally delivers sperm to the ejaculatory ducts. Severing or blocking the vas deferens provides sterility. While vasectomies are an exceedingly common form of male birth control, the procedure is generally considered permanent. A significant number of men who have had a vasectomy, subsequently wish to reverse the procedure to regain fertility. There are a variety of approaches to vasectomy reversal but all tend to be difficult, costly, and are not always successful. In light of this, there is a need for reliable reversible vasectomy devices and methods.

SUMMARY OF THE INVENTION

A first embodiment of the present invention provides a reversible vasectomy device for connecting severed ends of a vas deferens. The device includes a first and a second connector piece for attachment to the severed ends of the vas deferens. Each connector piece has an outer vas deferens attaching end and an opposite inner end. Each connector piece further has a passage defined from the outer end to the inner end. A midpiece has a first end portion that is connectable to the inner end of the first connector piece and a second end portion that is connectable to the inner end of the second connector piece. The first end portion has a passage defined therein. The midpiece has a vent extending from the passage to an exterior surface of the midpiece. When the first connector piece is connected to the first end portion and the second connector piece is connected to the second end portion, the passage in the first connector piece is in fluid communication with the passage in the first end portion of the midpiece and with the vent, but is not in fluid communication with the passage in the second connector piece.

The reversible vasectomy device may also include a first and a second sleeve element. Each sleeve element is receivable on the outer end of one of the connector pieces. The sleeve elements and the connector pieces cooperate to attach the ends of the vas deferens to the connector pieces.

In some embodiments, the outer end of each connector piece has a central tube and a coaxial outer wall with an annular space defined therebetween. One of the sleeve elements is received around the outer wall of each connector piece. The outer walls of each connector piece may include flexible elements that are pushed inwardly by the sleeve elements when the sleeve elements are received on the outer walls such that the flexible elements are urged against an outer surface of the vas deferens. In some versions, the outer walls of each connector piece have a plurality of generally longitudinal slits therein and the flexible elements are flexible fingers defined between the slits on the vas deferens attaching end of the connector pieces. The flexible fingers flex inwardly when the sleeve elements are received on the outer walls.

In some embodiments, each sleeve element has a stress relieving portion extending axially outwardly from the outer end of each connector piece. This stress relieving portion has a flexible outer wall surrounding an axial passage for receiving the vas deferens. The stress relieving portion may be a spiral shaped element.

In some embodiments of the reversible vasectomy device, a stress relieving element extends from the outer end of each connector piece and has a flexible outer wall surrounding an axial passage for receiving the vas deferens. This stress relieving element may be detachable from connector piece.

A reversible vasectomy device according to the present invention may include a second midpiece having a first end portion that is connectable to the first connector piece and a second end portion that is connectable to the second connector piece. The first end portion has a first passage defined therein and the second end portion has a second passage defined therein. The first passage is in fluid communication with the second passage such that when the first connector piece is connected to the first end portion and the second connector piece is connected to the second end portion, the passage in the first connector piece is in fluid communication the passage in the second connector piece.

According to a second embodiment of the present invention, a reversible vasectomy device has a first and a second connector piece for attachment to the severed ends of the vas deferens. Each connector piece has an outer vas deferens attaching end and an opposite inner end, and a passage defined from the outer end to the inner end. A midpiece has a first end portion that is connectable to the inner end of the first connector piece and a second end portion that is connectable to the inner end of the second connector piece. A first and a second sleeve element are receivable on the outer ends of one of the connector piece. The sleeve elements and the connector pieces cooperate to attach the ends of the vas deferens to the connector pieces. When the first connector piece is connected to the first end portion and the second connector piece is connected to the second end portion the passage in the first connector is not in fluid communication with the passage in the second connector piece.

A third embodiment of the present invention provides a reversible connection device for connecting severed ends of a body passage. The device includes a first and a second connector piece for attachment to the severed ends of the body passage. Each connector piece has an outer body passage attaching end, an opposite inner end, and a passage defined from the outer end to the inner end. A midpiece has a first end portion that is connectable to the inner end of the first connector piece and a second end portion that is connectable to the inner end of the second connector piece. A first and a second sleeve element are receivable on the outer ends of the connector pieces. The sleeve elements and the connector pieces cooperate to attach the ends of the body passage to the connector pieces. When the first connector piece is connected to the first end portion and the second connector piece is connected to the second end portion, the passage in the first connector piece is not in fluid communication with the passage in the second connector piece.

DETAILED DESCRIPTION OF THE PREFERRED EMBODIMENTS

Figure 1:
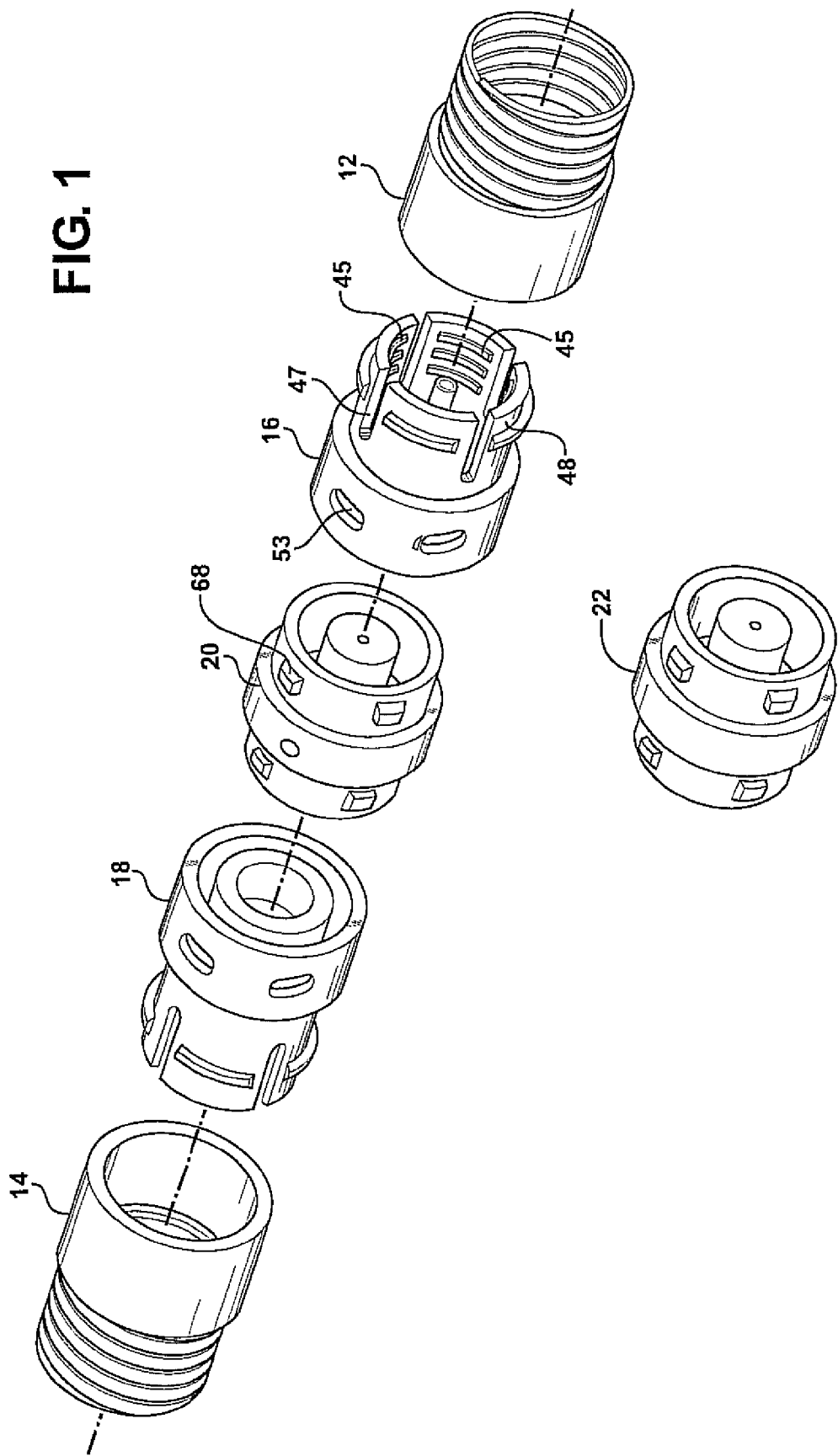
FIG. 1 is an exploded perspective view if a first embodiment of a reversible vasectomy device according to the present invention, showing a vented midpiece and an alternative pass-thru midpiece.

The present invention provides a device and method for providing long term reversible vasectomy procedures for male birth control. The various pieces of a first embodiment of a vasectomy device are shown in FIG. 1, arranged generally in assembly order. This embodiment includes two endmost pieces referred to as sleeve elements 12 and 14, a pair of connector pieces 16 and 18, and interchangeable midpieces 20 and 22. In a preferred embodiment of a method according to the present invention, the vas deferens is severed and then reconnected using a device according to an embodiment of the present invention. One severed end of the vas deferens, such as the epididymal end, is passed through the sleeve element 12 and connected to the connector piece 16. The other severed end of the vas deferens, such as the abdominal end, is passed through the center of the other sleeve element 14 and connected to the connector piece 18. The vas deferens ends are then reconnected to one another using either midpiece 20 or midpiece 22. Depending on which midpiece is used, the passage of sperm from one side to the other is either prevented (thereby providing sterility), or freely passable (thereby providing fertility). The details of the various pieces will now be described in more detail.

FIGS. 2-5 provide detailed views of the various pieces of the first embodiment of the vasectomy device according to the present invention. FIGS. 2-5 are drawn generally to scale for some embodiments of the present invention. As such, the relative dimensions of the various parts may be taken from these Figures. However, other embodiments may have different relative dimensions and shapes than illustrated.

Figure 2:
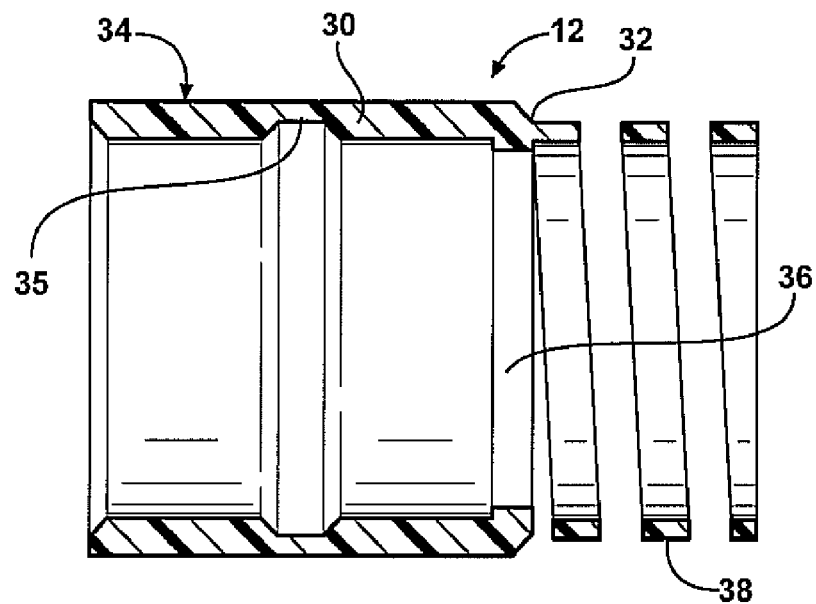
FIG. 2 is cross sectional view of a sleeve element that forms part of the first embodiment.

FIG. 2 provides a cross sectional view of an embodiment of the sleeve element 12. The sleeve element 12 has a generally cylindrical portion 30 that extends between an outer vas deferens receiving end 32 and a connection end 34. The vas deferens receiving end 32 has a vas deferens receiving opening 36 that may be somewhat smaller than the opening in the connection end 34. A stress relieving element 38 is connected to the vas deferens receiving end 32 of the generally cylindrical portion 30. In the illustrated embodiment, the stress relieving element takes the form of a spring-shaped or spiral-shaped support element that is generally coaxial with the vas deferens receiving opening 36. In use, the severed end of the vas deferens is passed through the stress relieving portion 38 and through the vas deferens receiving opening 36 in the vas deferens receiving end of the generally cylindrical portion 30. The stress relieving portion 32 may provide stress relief for the vas deferens and help to prevent the vas deferens from being bent at a sharp angle or being exposed to excess loading, thereby reducing the risk of tissue erosion. The stress relieving portion may be formed in other ways than illustrated, such as taking the form of a thin tube or mesh, or other forms.

Figure 3:
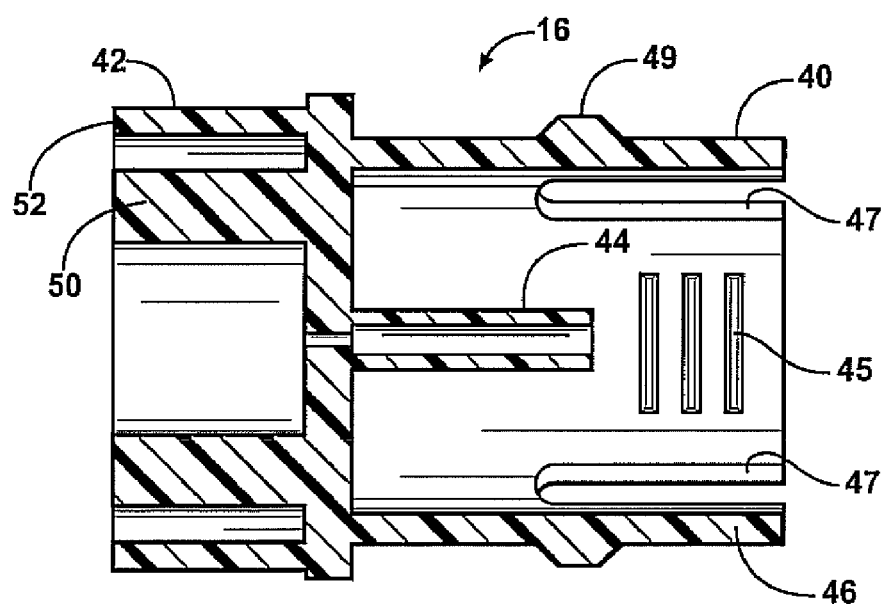
FIG. 3 is a cross sectional view of a connection piece that forms part of the first embodiment.

FIG. 3 provides a cross sectional view of the connector piece 16. The connector piece is generally cylindrically shaped with a pair of opposed ends 40 and 42. The outer end 40 is a vas deferens attaching end and is designed to receive the sleeve element 12 thereon in the direction shown in the exploded view of FIG. 1. The outer end 40 has a generally cylindrical central inner tube 44 surrounded by a coaxial outer generally cylindrical wall 46. The inner tube 44 is sized to cannulate the lumen of the severed end of the vas deferens. The muscular wall of the vas deferens is positioned between the outer surface of the inner tube 44 and the inner surface of the outer wall 46. Preferably, the outer end 40 includes flexible elements that may be urged inwardly by the sleeve element so as to grip the outer surface of the vas deferens. In the embodiment of FIG. 1, the outer end 40 has a plurality generally longitudinal slits 47 (four in this embodiment) defined therein. These slits 47 create flexible fingers 48 which serve as the flexible elements. As will be clear to those of skill in the art, when the sleeve element 12 is received on the outer end 40 of the connector piece, these fingers are flexed inwardly somewhat. The flexible elements 48 are sized and shaped so as to apply sufficient pressure to the vas deferens to retain it around the inner tube 44 without damaging or atrophying the end of the vas deferens. As shown in FIG. 1, the fingers 48 may have ridges or gripping elements 45 on the inner surface to improve the connection. This connection is preferably permanent with the vas deferens achieving a good bond with the connector piece 16. Alternative approaches to connecting the vas deferens to the device of the present invention may also be used, either alternatively or in addition to the gripping members. For example, glue or a bonding agent may be used or a shrinkable (such as heat-shrink) tube may be used to retain the end of the vas deferens. Examples of some exemplary approaches are discussed hereinbelow.

The outer end 40 of the connector piece may also have raised elements, such as ridge 49, on the outer surface for engagement with a corresponding recessed area 35 inside the sleeve element. As will be clear to those of skill in the art, other approaches for securely interconnecting the sleeve element and the connector piece may be used.

The inner end 42 of the connector piece 16 is designed to engage the midpiece 20 or the midpiece 22 so as to interconnect the connector piece with the corresponding connector piece 18. The inner end 42 includes a generally cylindrical inner wall 50 and a generally cylindrical outer wall 52 that are spaced apart.

As shown in FIG. 1, the two sleeve elements 12 and 14 may be identical to each other, and the two connector pieces 16 and 18 may be identical to each other, to reduce the complexity of manufacturing the device. Alternatively, the sleeve elements and/or connector pieces may be dissimilar such that they may only be used in a particular position.

Figure 4:
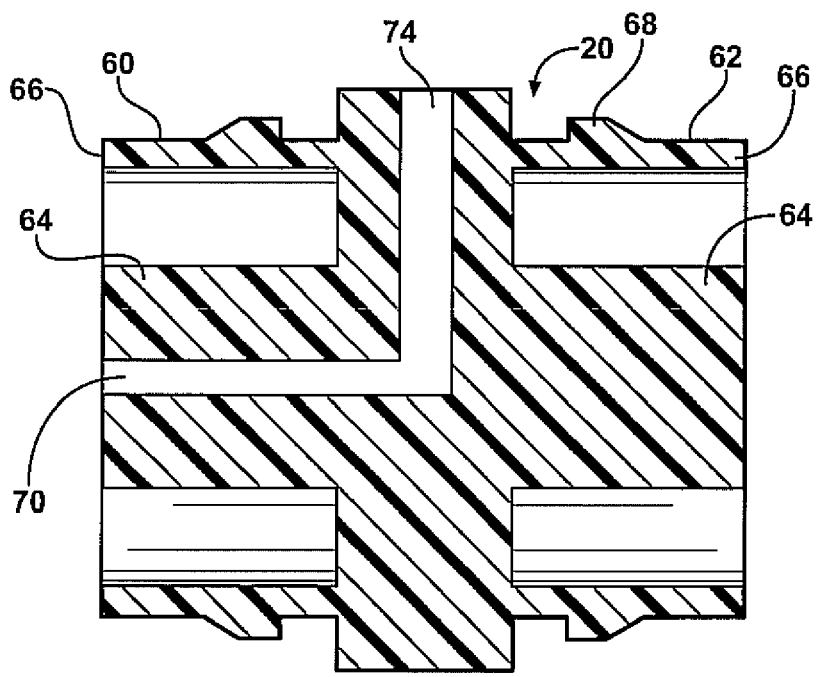
FIG. 4 is a cross sectional view of the vented midpiece that forms part of the first embodiment.

FIG. 4 provides a cross sectional view of the midpiece 20. The midpiece 20 has a pair of symmetrical ends 60 and 62 that sealingly interconnect with the inner ends 42 of the connector pieces 16 and 18 so as to interconnect the two connector pieces 16 and 18. Each end 60 and 62 of the midpiece 60 has an inner wall or element 64 that is generally cylindrical and an outer wall 66 that is generally cylindrical and spaced from the inner wall 64. In order to interconnect the connector piece 16 with the midpiece 20, the inner cylindrical wall 50 of the connector piece is positioned into the gap between the inner wall 64 and outer wall 66 and the outer wall 52 of the connector piece is received over the outer surface of the outer wall 66. As shown, locking teeth 68 may be provided on the outer surface of the outer wall 66 and the outer wall 52 of the connector piece may have corresponding receiving openings 53. As will be clear to those of skill in the art, other approaches to interconnection the connection pieces and the midpiece may also be used. For example, a ridge and recess may be provided similar to the connection between the sleeve element 12 and connector piece 16.

As shown in the cross-sectional view of FIG. 4, the inner wall 64 at one end of the midpiece 20 each have a central passage 70 while the other end does not have a passage. As is clear in the Figure, the two ends are not in fluid communication with one another Instead, the passage 70 is in fluid communication with one or more vents 74 which pass from the central passage 70 to the outer perimeter of the midpiece 20. In use, this end of the midpiece 20 is connected to the epididymal end of the vas deferens such that sperm passes through the passage 70 and out through the vent 74. The other, abdominal, end of the vas deferens is in communication with end of the midpiece that lacks a passage. Therefore, the passage in the connector piece is closed off such that sperm in the passage 70 does not communicate to the other passage. The vents 74 prevent back pressure on the epididymis, thereby helping to maintain the function of the reproductive system in case reversal is later desired. An alternative embodiment may eliminate the vent, or provide a vent of different configuration. The provision of a vent to prevent epididymal backpressure is preferred.

The midpiece 20 acts as a vasectomy device and provides sterility. In use, the surgeon severs the vas deferens and interconnects the epididymal end to the connector piece 16 using a sleeve element and connects the other, abdominal, end of the vas deferens to the connector piece 18. The pieces 16 and 18 are then interconnected with the midpiece 20 to provide sterility. If the patient later wishes to reverse the vasectomy, the surgeon then may disconnect the pieces 16 and 18 from the midpiece 20 and replace the midpiece 20 with a pass-thru midpiece 22.

Figure 5:
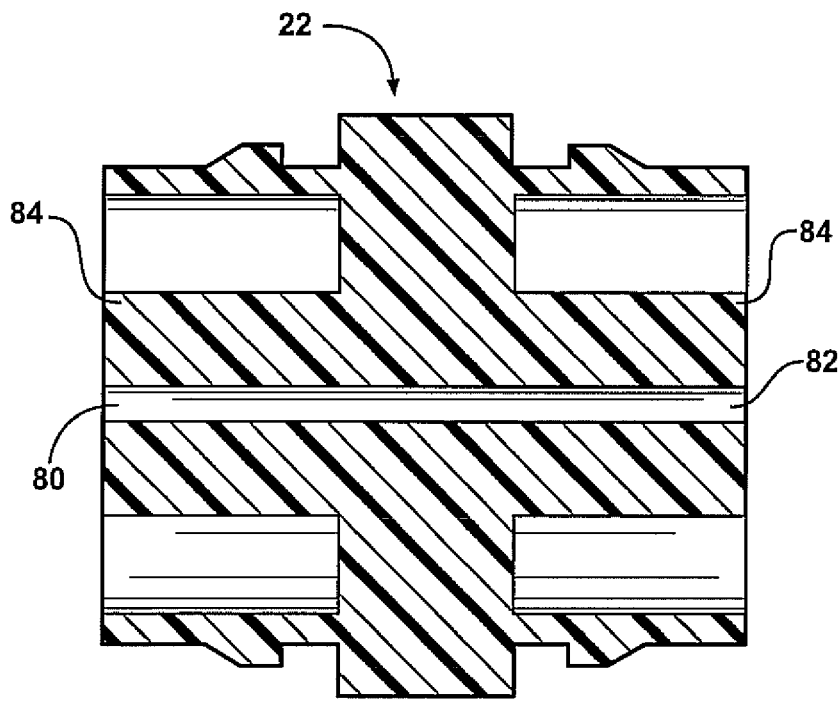
FIG. 5 is a cross sectional view of the alternative pass-thru midpiece that may be used with the first embodiment.

A cross sectional view of the pass-thru midpiece 22 is shown in FIG. 5. The midpiece 22 is very similar to the midpiece 20 except that passages 80 and 82 in the inner walls 84 and 86 are in fluid communication with one another such that sperm that enters the passage 80 passes on through the passage 82 and fertility is restored.

Figure 6:
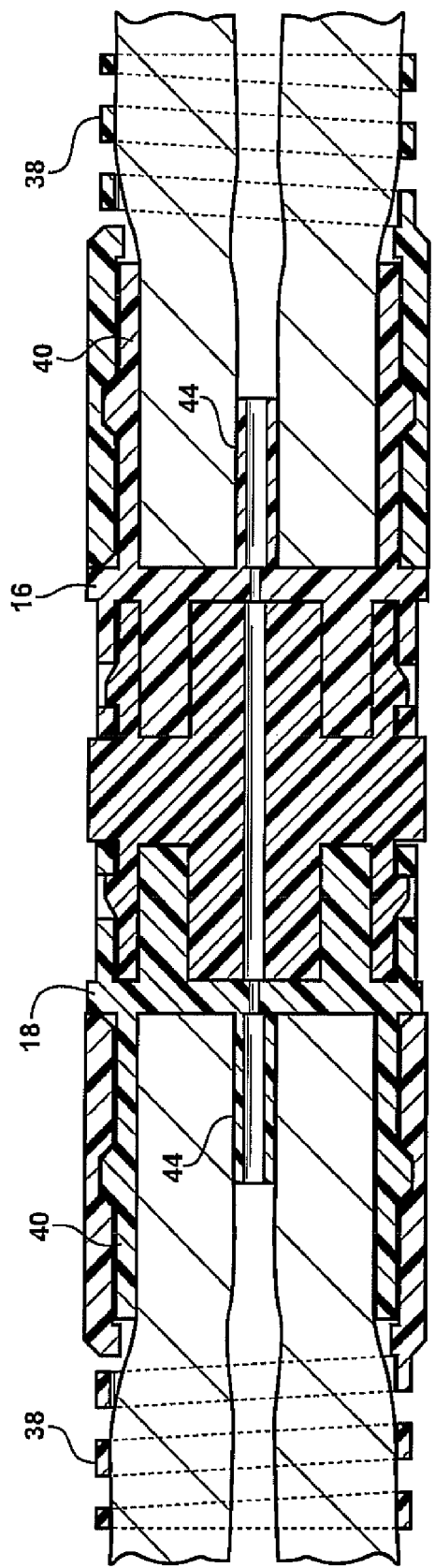
FIG. 6 is a cross sectional view of the first embodiment of the reversible vasectomy device with the device assembled and joining the severed ends of the vas deferens with the pass-thru midpiece in use.

FIG. 6 provides a cross sectional view of the device of FIG. 1 assembled so as to join the severed ends of a vas deferens. As shown, the inner tubes 44 of the connector pieces 16 and 18 cannulate the lumen of the vas deferens and the outer walls 40 engage the outer surface of the vas deferens. The stress relieving portions 38 extend outwardly and support the vas deferens.

As will be clear to those of skill in the art, numerous alternations may be made to the illustrated embodiment without departing from the scope or teaching of the present invention. A few examples will be discussed. The tube 44 may be formed out of various materials and with various textures, or may be replaced with a stent or a stent like device. It is preferred that the tube or stent be formed of a flexible material to reduce erosion of the vas deferens. The tube or stent 44 may also be a separate piece that is first inserted into the lumen and then assembled to the remainder of the device. As another alternative, the outer wall 40 and/or the sleeve element 12 may be altered in various ways, or eliminated, while still allowing the present invention to function to join the severed ends.

Figure 7:
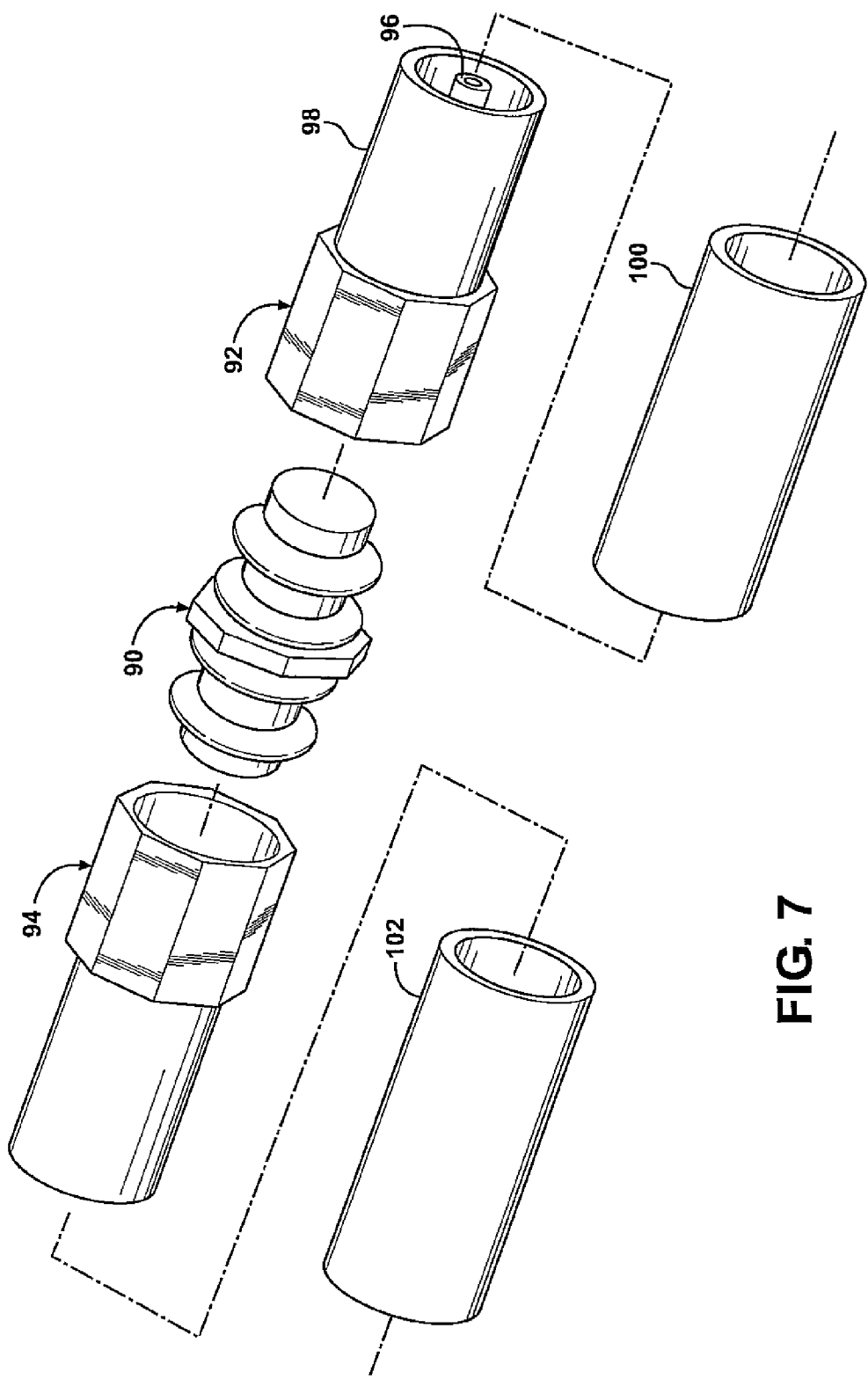
FIG. 7 is an exploded perspective view of an alternative embodiment of a device according to the present invention.

As another alternative, the design of the midpiece may be changed such as having a different wall configuration or using sealing elements, threads, or other approaches. As mentioned previously, the severed ends of the vas deferens may be joined to the connector pieces in various ways, such as using a bonding agent, shrinkable tubing, etc. FIG. 7 illustrates an alternative embodiment of the present invention having a different midpiece 90 and different connector pieces 92 and 94. The connector pieces have a central tube 96 to cannulate the lumen and an outer wall 98 that surrounds the severed end. Shrinkable tubing, such as tubing that is shrunk by application of heat or an activating agent, is shown at 100 and 102. This tubing fits over the outer ends of the connector pieces and serves both to connect the severed ends and to provide support and stress relief. The midpiece 90 differs in that it has a pair of ends with sealing elements that are received in corresponding openings in the connector pieces. Other approaches will be clear to those of skill in the art. For example, the use of connector pieces and shrinkable tubing may be combined with the midpiece approach of FIG. 1. Further, shrinkable tubing, adhesive bonding and/or mechanical attachment may be combined. Also, other approaches to mechanical attachment may be used, either in combination with or instead of the approaches described herein. One alternative is to stitch the ends of the vas deferens to a connector piece, which then attaches to a midpiece.

Figure 8:
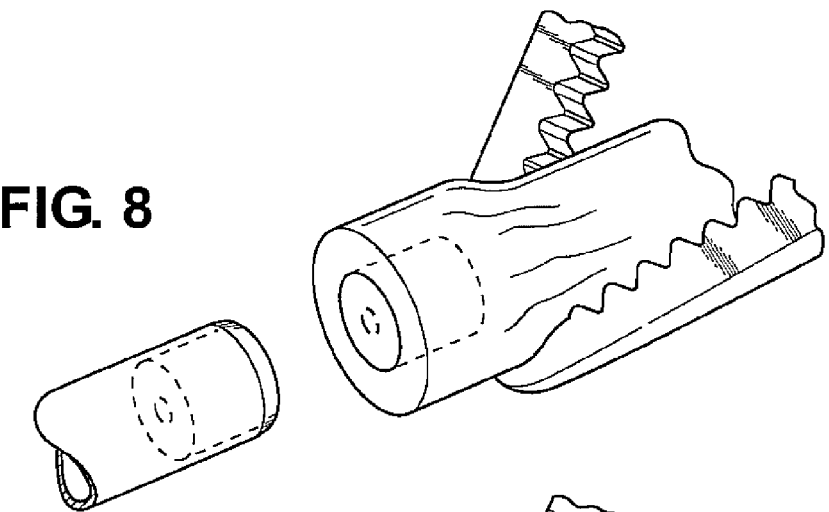
FIG. 8 is a view of the end of a vas deferens that has been punched to expand the opening.
Figure 9:
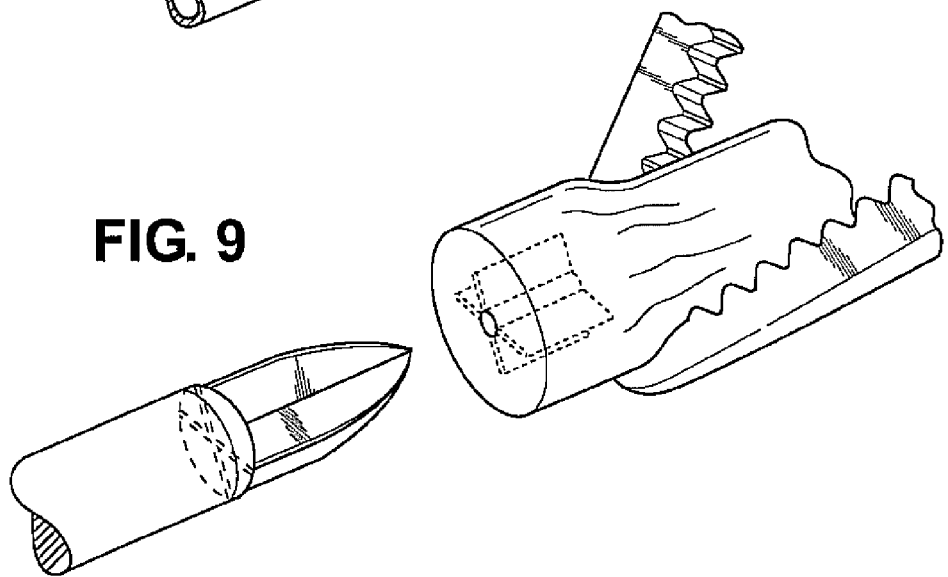
FIG. 9 is a view similar to FIG. 8, where the end is slit.
Figure 10:
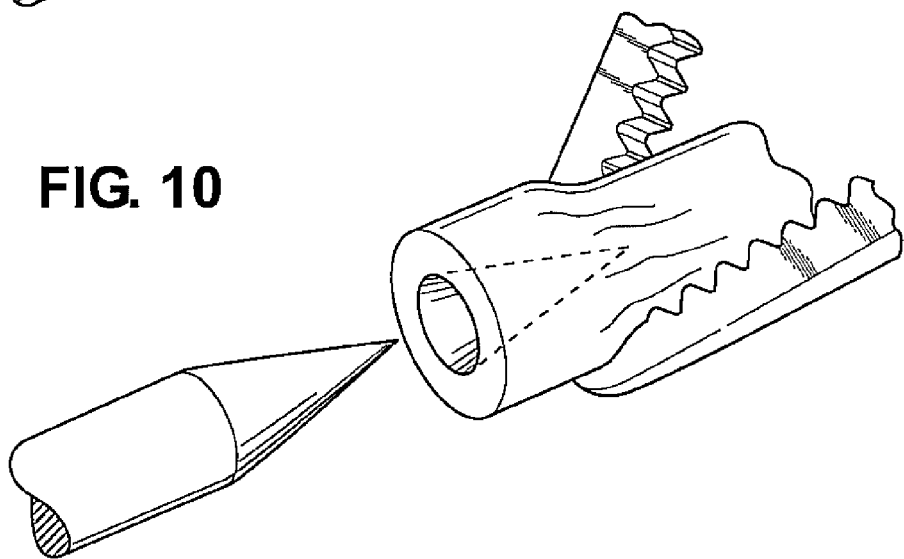
FIG. 10 is a view similar to FIGS. 8 and 9 where the end has been reshaped.

When the device of the present invention, one important step is positioning the inner tube of the connector piece into the lumen of the severed end. FIGS. 8-10 illustrate some approaches for enlarging the end to provide easier assembly. In FIG. 8, the end of the lumen is punched out to remove some of the musculature and the fit over the inner tube. In FIG. 9, the end of the lumen is slit to allow it to expand. In FIG. 10, the end of the lumen has been expanded or stretched such as by using a tapered tool. With any of these approaches, the inner tube may be made somewhat larger, which may be beneficial.

As known to those of skill in the art, the human vas deferens is quite small. As such, the device illustrated herein is also small. In some embodiments, the inner tube 44 has an outer diameter in the range of 0.7 to 0.8 mm and a length in the range of 2 to 3 mm. The outer wall 40 has an inner diameter in the range of 3 to 4 mm and a length in the range of 2 to 4 mm. The stress relieving portion 38 extends outwardly for a distance in the range of 2 to 3 mm. Other dimensions are proportionate.

The present invention may have use in other applications, such as non-human reversible vasectomies, use in a fallopian tube or use in other body passages. The size of the device for other applications will also differ, typically being larger. Also, these devices may lack the vent arrangement.

While not illustrated, it is preferred that the outer surfaces of the various components of the present invention include gripping areas, such as flattened areas, to allow easier manipulation of the various components during a vasectomy procedure.

As will be clear to those of skill in the art, the components of the present invention may be formed of various materials, with biocompatible materials preferred. In some embodiments, the components are formed of a polymer material that is somewhat flexible if sufficiently thin and relatively rigid where parts are thicker. This allows the components to be somewhat flexible in areas where needed and more rigid where needed. For example, it is preferred that the stress relieving portion be somewhat flexible to allow stress relief while the snap together portions are preferably more rigid. The luminal portion of the connector pieces that goes into the vas deferens may also be somewhat flexible. This may reduce erosion of the vas deferens. One material that may be used is PEEK (Polyetheretherketone).

As will be clear to those of skill in the art, the embodiments of the present invention disclosed herein may be altered in various ways without departing from the scope or teaching of the present invention. For example, some portions may be oval or more squared off rather than the generally circular configuration illustrated. Further, the configuration of the various tabs and teeth that form the locking connections may be formed in other ways, may be bigger or smaller, tabs and teeth may be reversed, and other changes may be made without substantially altering the function of the parts. Other changes will also be clear to those of skill in the art. It is the following claims, including all equivalents, which define the scope of the present invention.

The invention claimed is:

1. A reversible vasectomy device for connecting severed ends of a vas deferens, the device comprising:
   a first and a second connector piece for attachment to the severed ends of the vas deferens, each connector piece having an outer vas deferens attaching end and an opposite inner end, each connector piece further having a passage defined from the outer end to the inner end; and
   a midpiece having a first end portion that is connectable to the inner end of the first connector piece and a second end portion that is connectable to the inner end of the second connector piece, the first end portion having a passage defined therein, the midpiece further having a vent extending from the passage to an exterior surface of the midpiece;
   wherein when the first connector piece is connected to the first end portion and the second connector piece is connected to the second end portion, the passage in the first connector piece is in fluid communication with the passage in the first end portion of the midpiece and with the vent, but is not in fluid communication with the passage in the second connector piece.

2. The reversible vasectomy device of claim 1, further comprising a first and a second sleeve element, each sleeve element being receivable on the outer end of one of the connector pieces, the sleeve elements and the connector pieces cooperating to attach the ends of the vas deferens to the connector pieces.

3. The reversible vasectomy device of claim 2, wherein the outer end of each connector piece has a central tube and a coaxial outer wall with an annular space defined therebetween, one of the sleeve elements being received around the outer wall of each connector piece.

4. The reversible vasectomy device of claim 3, wherein the outer walls of each connector piece include flexible elements that are pushed inwardly by the sleeve elements when the sleeve elements are received on the outer walls such that the flexible elements are urged against an outer surface of the vas deferens.

5. The reversible vasectomy device of claim 4, wherein the outer walls of each connector piece have a plurality of generally longitudinal slits therein, the flexible elements comprising flexible fingers defined between the slits on the vas deferens attaching end of the connector pieces, the flexible fingers flexing inwardly when the sleeve elements are received on the outer walls.

6. The reversible vasectomy device of claim 2, wherein each sleeve element has a stress relieving portion extending axially outwardly from the outer end of each connector piece, the stress relieving portion having a flexible outer wall surrounding an axial passage for receiving the vas deferens.

7. The reversible vasectomy device of claim 6, wherein the stress relieving portion comprises a spiral shaped element.

8. The reversible vasectomy device of claim 1, further comprising a stress relieving element extending from the outer end of each connector piece, the stress relieving element having a flexible outer wall surrounding an axial passage for receiving the vas deferens.

9. The reversible vasectomy device of claim 8, wherein the stress relieving element is detachable from connector piece.

10. The reversible vasectomy device of claim 1, wherein the midpiece is a first midpiece, the device further comprising a second midpiece that is interchangeable with the first midpiece, the second midpiece having a first end portion that is connectable to the first connector piece and a second end portion that is connectable to the second connector piece, the first end portion of the second midpiece having a first passage defined therein and the second end portion of the second midpiece having a second passage defined therein, the first passage being in fluid communication with the second passage;
    wherein when the first connector piece is connected to the first end portion of the second midpiece and the second connector piece is connected to the second end portion of the second midpiece, the passage in the first connector piece is in fluid communication the passage in the second connector piece.

11. A reversible vasectomy device for connecting severed ends of a vas deferens, the device comprising:
    a first and a second connector piece for attachment to the severed ends of the vas deferens, each connector piece having an outer vas deferens attaching end and an opposite inner end, each connector piece further having a passage defined from the outer end to the inner end;
    a midpiece having a first end portion that is connectable to the inner end of the first connector piece and a second end portion that is connectable to the inner end of the second connector piece; and
    a first and a second sleeve element, each sleeve element being receivable on the outer end of one of the connector pieces, the sleeve elements and the connector pieces cooperating to attach the ends of the vas deferens to the connector pieces with each sleeve element being at least partially disposed around an outer surface of one of the connector pieces;
    wherein when the first connector piece is connected to the first end portion and the second connector piece is connected to the second end portion, the passage in the first connector is not in fluid communication with the passage in the second connector piece.

12. A reversible vasectomy device for connecting severed ends of a vas deferens, the device comprising:
    a first and a second connector piece for attachment to the severed ends of the vas deferens, each connector piece having an outer vas deferens attaching end and an opposite inner end, each connector piece further having a passage defined from the outer end to the inner end;
    a midpiece having a first end portion that is connectable to the inner end of the first connector piece and a second end portion that is connectable to the inner end of the second connector piece; and a first and a second sleeve element, each sleeve element being receivable on the outer end of one of the connector pieces, the sleeve elements and the connector pieces cooperating to attach the ends of the vas deferens to the connector pieces;

wherein the outer end of each connector piece has a central tube and a coaxial outer wall with an annular space defined therebetween, one of the sleeve elements being received around the outer wall of each connector piece;

wherein when the first connector piece is connected to the first end portion and the second connector piece is connected to the second end portion, the passage in the first connector is not in fluid communication with the passage in the second connector piece.

13. The reversible vasectomy device of claim 12, wherein the outer walls of each connector piece include flexible elements that are pushed inwardly by the sleeve elements when the sleeve elements are received on the outer walls such that the flexible elements are urged against an outer surface of the vas deferens.

14. The reversible vasectomy device of claim 13, wherein the outer walls of each connector piece have a plurality of generally longitudinal slits therein, the flexible elements comprising flexible fingers defined between the slits on the vas deferens attaching end of the connector pieces, the flexible fingers flexing inwardly when the sleeve elements are received on the outer walls.

15. A reversible vasectomy device, for connecting severed ends of a vas deferens, the device comprising:

a first and a second connector piece for attachment to the severed ends of the vas deferens, each connector piece having an outer vas deferens attaching end and an opposite inner end, each connector piece further having a passage defined from the outer end to the inner end;

a midpiece having a first end portion that is connectable to the inner end of the first connector piece and a second end portion that is connectable to the inner end of the second connector piece; and a first and a second sleeve element, each sleeve element being receivable on the outer end of one of the connector pieces, the sleeve elements and the connector pieces cooperating to attach the ends of the vas deferens to the connector pieces;

wherein each sleeve element has a stress relieving portion extending axially outwardly from the outer end of each connector piece, the stress relieving portion having a flexible outer wall surrounding an axial passage for receiving the vas deferens;

wherein when the first connector piece is connected to the first end portion and the second connector piece is connected to the second end portion, the passage in the first connector is not in fluid communication with the passage in the second connector piece.

16. The reversible vasectomy device of claim 15, wherein the stress relieving portion comprises a spiral shaped element.

17. A reversible vasectomy device for connecting severed ends of a vas deferens, the device comprising:

a first and a second connector piece for attachment to the severed ends of the vas deferens, each connector piece having an outer vas deferens attaching end and an opposite inner end, each connector piece further having a passage defined from the outer end to the inner end;

a midpiece having a first end portion that is connectable to the inner end of the first connector piece and a second end portion that is connectable to the inner end of the second connector piece, the midpiece further having a passage defined in one end portion and a vent extending from the passage to an exterior surface of the midpiece; and a first and a second sleeve element, each sleeve element being receivable on the outer end of one of the connector pieces, the sleeve elements and the connector pieces cooperating to attach the ends of the vas deferens to the connector pieces;

wherein when the first connector piece is connected to the first end portion and the second connector piece is connected to the second end portion, the passage in the first connector is not in fluid communication with the passage in the second connector piece.

18. A reversible connection device for connecting severed ends of a body passage, the device comprising:

a first and a second connector piece for attachment to the severed ends of the body passage, each connector piece having an outer body passage attaching end and an opposite inner end, each connector piece further having a passage defined from the outer end to the inner end;

a midpiece having a first end portion that is connectable to the inner end of the first connector piece and a second end portion that is connectable to the inner end of the second connector piece; and a first and a second sleeve element, each sleeve element being receivable on the outer end of one of the connector pieces, the sleeve elements and the connector pieces cooperating to attach the ends of the body passage to the connector pieces with each sleeve element being at least partially disposed around an outer surface of one of the connector pieces;

wherein when the first connector piece is connected to the first end portion and the second connector piece is connected to the second end portion, the passage in the first connector piece is not in fluid communication with the passage in the second connector piece.

* * * * *

UNITED STATES PATENT AND TRADEMARK OFFICE
CERTIFICATE OF CORRECTION

| | | |
|---|---|---|
| PATENT NO. | : 8,161,973 B2 | Page 1 of 1 |
| APPLICATION NO. | : 12/206132 | |
| DATED | : April 24, 2012 | |
| INVENTOR(S) | : J C Trussell | |

It is certified that error appears in the above-identified patent and that said Letters Patent is hereby corrected as shown below:

In the Specifications:
At column 2, line number 18, after from, insert --each--.

At column 2, line number 30, after communication, insert --with--.

At column 2, line number 42, delete "piece", insert --pieces--.

At column 3, line number 3, delete "if", insert --of--.

At column 5, line number 15, delete "interconnection", insert --interconnecting--.

At column 5, line number 23, after another, insert --.--.

At column 5, line number 30, before end, insert --the--.

At column 6, line number 31, delete "maybe", insert --may be--.

At column 6, line number 35, delete "when", insert --with--.

At column 6, line number 40, after and, delete "the", insert --to--.

In the Claims:
At column 8, line number 18, Claim 9, after from, insert --the--.

At column 8, line number 34, Claim 10, after communication, insert --with--.

Signed and Sealed this
Twenty-fifth Day of September, 2012

David J. Kappos
*Director of the United States Patent and Trademark Office*